(12) United States Patent
Grossman et al.

(10) Patent No.: US 10,040,952 B2
(45) Date of Patent: Aug. 7, 2018

(54) COATING COMPOSITIONS COMPRISING POLYMERS HAVING TITANIUM/OXYGEN OR SILICON/OXYGEN BACKBONES

(71) Applicant: Allied Bioscience, Inc., Dallas, TX (US)

(72) Inventors: Craig Grossman, Point Roberts, WA (US); Mai Ngo, Tucson, AZ (US); Ronald Wysocki, Tucson, AZ (US)

(73) Assignee: ALLIED BIOSCIENCE, INC., Dallas, TX (US)

( * ) Notice: Subject to any disclaimer, the term of this patent is extended or adjusted under 35 U.S.C. 154(b) by 0 days.

(21) Appl. No.: 15/432,352

(22) Filed: Feb. 14, 2017

(65) Prior Publication Data

US 2017/0158873 A1 Jun. 8, 2017

Related U.S. Application Data

(63) Continuation of application No. 13/448,325, filed on Apr. 16, 2012, now Pat. No. 9,757,769, and a continuation of application No. 15/432,334, filed on Feb. 14, 2017, now Pat. No. 9,855,584.

(60) Provisional application No. 61/489,630, filed on May 24, 2011, provisional application No. 61/476,233, filed on Apr. 15, 2011.

(51) Int. Cl.

| | |
|---|---|
| *C09D 5/14* | (2006.01) |
| *C09D 7/12* | (2006.01) |
| *C09D 185/00* | (2006.01) |
| *A01N 55/00* | (2006.01) |
| *A01N 55/02* | (2006.01) |
| *C09D 7/63* | (2018.01) |

(52) U.S. Cl.
CPC ........... *C09D 5/14* (2013.01); *A01N 55/00* (2013.01); *A01N 55/02* (2013.01); *C09D 7/1233* (2013.01); *C09D 7/63* (2018.01); *C09D 185/00* (2013.01)

(58) Field of Classification Search
None
See application file for complete search history.

(56) References Cited

U.S. PATENT DOCUMENTS

| | | | |
|---|---|---|---|
| 4,721,511 A * | 1/1988 | Kupits | D06M 13/188 424/404 |
| 5,569,732 A | 10/1996 | Nohr et al. | |
| 6,037,289 A | 3/2000 | Chopin et al. | |
| 6,180,548 B1 | 1/2001 | Taoda et al. | |

(Continued)

FOREIGN PATENT DOCUMENTS

| | | |
|---|---|---|
| CN | 1538937 | 10/2004 |
| CN | 101827650 | 9/2010 |

(Continued)

OTHER PUBLICATIONS

Notice of Acceptance dated Jun. 28, 2017 in Australian Application No. 2017202598.

(Continued)

*Primary Examiner* — Michael P Rodriguez
(74) *Attorney, Agent, or Firm* — Snell & Wilmer L.L.P.

(57) ABSTRACT

A method to prepare a self-decontaminating surface, where that method includes disposing a first coating on a surface, where that first coating comprises an organosilane, and disposing a second coating over the first coating, where the second coating comprises $TiO_2$.

20 Claims, 6 Drawing Sheets

OPTICAL IMAGE USING TRANSMISSION GEOMETRY WITH 10x OBJECTIVE
IMAGE SIZE: 2.4mm x 1.8 mm

(56) References Cited

U.S. PATENT DOCUMENTS

| | | | |
|---|---|---|---|
| 6,228,480 | B1 | 5/2001 | Kimura et al. |
| 6,432,191 | B2 | 8/2002 | Schutt |
| 6,436,085 | B1 | 8/2002 | Lauer |
| 7,262,158 | B1 | 8/2007 | Lukenbach et al. |
| 7,541,048 | B2 | 6/2009 | DeWitt et al. |
| 7,763,565 | B2 | 7/2010 | Fu et al. |
| 2003/0127207 | A1 | 7/2003 | Clark et al. |
| 2004/0023824 | A1 | 2/2004 | Zuechner et al. |
| 2005/0008613 | A1 | 1/2005 | Peterson et al. |
| 2005/0008763 | A1* | 1/2005 | Schachter ............ A61L 29/085 427/2.24 |
| 2005/0214483 | A1 | 9/2005 | Fujieda et al. |
| 2007/0065475 | A1* | 3/2007 | Elfersy ................. A01N 33/12 424/405 |
| 2007/0167551 | A1 | 7/2007 | Goodwin et al. |
| 2007/0275101 | A1 | 11/2007 | Lu |
| 2008/0305153 | A1 | 12/2008 | Wang et al. |
| 2009/0062111 | A1 | 3/2009 | Fu et al. |
| 2009/0118152 | A1 | 5/2009 | Lam et al. |
| 2009/0209665 | A1 | 8/2009 | Fu et al. |
| 2009/0274914 | A1 | 11/2009 | Hoshi et al. |
| 2009/0298967 | A1 | 12/2009 | Taylor et al. |
| 2010/0028462 | A1 | 2/2010 | Bolkan |
| 2010/0055028 | A1 | 3/2010 | Scott et al. |
| 2010/0075298 | A1 | 3/2010 | Creek et al. |
| 2010/0144518 | A1 | 6/2010 | Scott et al. |
| 2010/0267550 | A1 | 10/2010 | Fu et al. |
| 2010/0292185 | A1 | 11/2010 | Burns et al. |
| 2011/0274767 | A1 | 11/2011 | Kato et al. |
| 2012/0291667 | A1 | 11/2012 | Geoffrion et al. |
| 2013/0122074 | A1 | 5/2013 | Kerrod et al. |
| 2017/0088717 | A1 | 3/2017 | Grossman |

FOREIGN PATENT DOCUMENTS

| | | |
|---|---|---|
| CN | 101998979 | 3/2011 |
| EP | 0923988 | 9/2008 |
| KR | 1020080093483 | 10/2008 |
| KR | 1020080110268 | 12/2008 |
| KR | 1020090110672 | 10/2009 |
| WO | WO 2009029856 | 3/2009 |
| WO | WO 2009057046 | 5/2009 |

OTHER PUBLICATIONS

Notice of Allowance dated Jul. 13, 2017 in U.S. Appl. No. 13/448,325.
Final Office Action dated May 4, 2017 in U.S. Appl. No. 13/448,325.
Notification of Reexamination dated May 25, 2017 in Chinese Application No. 201280026252.0.
Examination Report dated Jun. 2, 2017 in Australian Application No. 2017202598.
Decision to Grant dated Feb. 14, 2017 in Russian Application No. 2013150917/05.
Grossman, et al., U.S. Appl. No. 15/432,334, filed Feb. 14, 2017 and entitled "Methods of Preparing Self-Decontaminating Surfaces Using Quaternary Silanes and Titanium Anatase Sol".
Grossman, et al., U.S. Appl. No. 15/432,363, filed Feb. 14, 2017 and entitled "Methods of Preparing Reactive Mixtures of Quaternary Silanes and Titanium(IV)Alkoxides and Polymers Therefrom".
International Search Report and Written Opinion dated Jul. 17, 2012 in Application No. PCT/US2012/033844.
Restriction Requirement dated Apr. 17, 2013 in U.S. Appl. No. 13/708,613.
Restriction Requirement dated Oct. 2, 2013 in U.S. Appl. No. 13/448,325.
International Preliminary Report on Patentability dated Oct. 15, 2013 in Application No. PCT/US2012/033844.
Office Action dated Nov. 19, 2013 in U.S. Appl. No. 13/448,325.
International Search Report and Written Opinion dated Mar. 26, 2014 in Application No. PCT/US2013/073878.
Office Action dated Apr. 8, 2014 in U.S. Appl. No. 13/708,613.
Final Office Action dated Sep. 17, 2014 in U.S. Appl. No. 13/448,325.
Office Action dated Oct. 24, 2014 in U.S. Appl. No. 13/708,613.
Extended European Search Report dated Oct. 28, 2014 in European Application No. 12771919.3.
Office Action dated Dec. 11, 2014 in Chinese Application No. 201280026252.0.
Final Office Action dated Mar. 17, 2015 in U.S. Appl. No. 13/708,613.
Office Action dated Mar. 27, 2015 in U.S. Appl. No. 13/448,325.
International Preliminary Report on Patentability dated Jun. 9, 2015 in Application No. PCT/US2013/073878.
Office Action dated Aug. 4, 2015 in Chinese Application No. 201280026252.0.
Office Action dated Sep. 3, 2015 in U.S. Appl. No. 13/708,613.
Office Action dated Oct. 20, 2015 in U.S. Appl. No. 13/448,325.
Office Action dated Feb. 6, 2016 in Chinese Application No. 201280026252.0.
Office Action dated Mar. 17, 2016 in Russian Application No. 2013150917.
Final Office Action dated Jun. 1, 2016 in U.S. Appl. No. 13/708,613.
Patent Examination Report No. 1 dated Jun. 3, 2016 in Australian Application No. 2012242454.
Rejection Decision dated Jul. 6, 2016 in Chinese Application No. 201280026252.0.
Office Action dated Jul. 15, 2016 in Russian Application No. 2013150917.
Notice of Allowance dated Oct. 31, 2016 in U.S. Appl. No. 13/708,613.
Office Action dated Jan. 26, 2017 in U.S. Appl. No. 13/448,325.
Notice of Acceptance dated Feb. 8, 2017 in Australian Application No. 2012242454.
AEGIS, Mater Label—AEM 5772-5 Antimicrobial—A Silane Quaternary Ammonium Salt, 9 pages, 2006.
AEGIS, AEM 5772-5 Antimicrobial—A Silane Quaternary Ammonium Salt, 1 page, 2009.
AGIS Environments, "Material Safety Data Sheet," AEM 5772 Antimicrobial (72% Active Concentrate), p. 1-7, USA, 2004.
Su et al., "Sol-gel preparation and photocatalysis of titanium dioxide," Catalysis Today 96, 2004, pp. 119-126, Elsevier B.V.
Liu et al., "Synthesis and Characterization of Titania Prepared by Using a Photoassisted Sol-Gel Method," Langmuir 2003, pp. 3001-3005.
USPTO; Notice of Allowance dated Oct. 5, 2017 in U.S. Appl. No. 15/432,334.
USPTO; Non-Final Office Action dated Oct. 10, 2017 in U.S. Appl. No. 15/432,363.
EP Examination Report dated Aug. 10, 2017 in EP Application No. 12771919.3.
Office Action dated Jun. 23, 2017 in Mexican Application No. MX/a/2013/012000.

* cited by examiner

OPTICAL IMAGE USING TRANSMISSION GEOMETRY WITH 10x OBJECTIVE
IMAGE SIZE: 2.4mm x 1.8 mm ns and methods, the invention may be combined in any suitable manner in one or
COATING COMPOSITIONS COMPRISING POLYMERS HAVING TITANIUM/OXYGEN OR SILICON/OXYGEN BACKBONES

CROSS-REFERENCE TO RELATED APPLICATIONS

This application is a continuation of, claims priority to and the benefit of, U.S. Ser. No. 13/448,325, filed Apr. 16, 2012 and entitled COMPOSITION AND METHOD TO FORM A SELF-DECONTAMINATING SURFACE. The '325 application claims priority to, and the benefit of, U.S. Provisional Application No. 61/476,233, filed Apr. 15, 2011 and entitled COMPOSITION AND METHOD TO FORM A SELF DECONTAMINATION SURFACE, and U.S. Provisional Application No. 61/489,630, filed May 24, 2011 and entitled COMPOSITION AND METHOD TO FORM A SELF DECONTAMINATING SURFACE. All of the aforementioned applications are hereby incorporated by reference in their entirety.

FIELD

Embodiments generally relate a chemical composition and a method to form a self decontaminating surface. In certain embodiments, the chemical composition comprises a photocatalyst. In certain embodiments, the photocatalyst comprises a titanium oxide moiety. In certain embodiments, the chemical composition is applied as an electrostatic deposit of a film formed of titanium dioxide moieties.

BACKGROUND

Titanium oxide (e.g., $TiO_2$) is a nontoxic substance widely used in paints, paper, plastics, and toothpaste. It is known in the art that an alkali hydroxide can be added to an aqueous titanium salt solution to produce an amorphous titanium peroxide sol. The titanium peroxide sol can be reacted with an aqueous hydrogen peroxide solution to produce an amorphous titanium peroxide sol, which is then heated to high temperatures to obtain anatase titanium oxide.

Current methods for preparing sheets, coatings, or films comprising titanium oxide require that the titanium oxide particles be sintered at high temperatures (e.g., 200 to 400 degrees Celsius) in order to firmly support the titanium oxide on a substrate. Using these prior art methods, a titanium oxide compound is deposited onto a substrate, and then baked at approximately 200-400 degrees Celsius to fixedly set the compound on the substrate. The requirement of such high temperatures to cure the titanium oxide limits its utility, such as use of titanium dioxide to create self-decontaminating surfaces by retailers or consumers.

Accordingly, it would be an advance in the art to develop or use a new titanium oxide sheet, coating, or film deposition.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION

Figure 1:
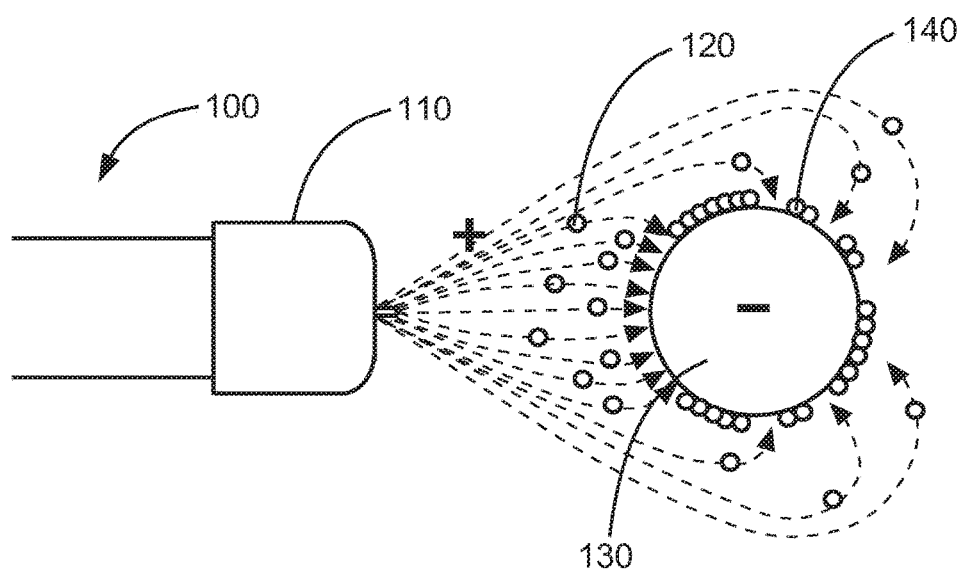
FIG. 1 illustrates one embodiment of a electrostatic spray apparatus.

The invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Titanium dioxide occurs in nature as well-known minerals rutile, anatase and brookite, and additionally as two high pressure forms, a monoclinic baddeleyite-like form and an orthorhombic α-PbO2-like form, both found recently at the Ries crater in Bavaria. The most common form is rutile, which is also the most stable form. Anatase and brookite both convert to rutile upon heating. Rutile, anatase and brookite all contain six coordinated titanium.

Titanium dioxide has numerous modifications—in addition to rutile, anatase and brookite there are three metastable forms produced synthetically (monoclinic, tetragonal and orthorombic), and high pressure forms (α-PbO2-like, baddeleyite-like and cotunnite-like):

Oxidation—loss of electrons or an increase in oxidation state by a molecule, atom or ion. Substances that have the ability to oxidize other substances are said to be oxidative or oxidizing and are known as oxidizing agents, oxidants, or oxidizers. Put another way, the oxidant removes electrons from another substance, and is thus itself reduced. And, because it "accepts" electrons, it is also called an electron acceptor.

In chemistry, photocatalysis is the acceleration of a photoreaction in the presence of a catalyst. In catalyzed photolysis, light is absorbed by an adsorbed substrate. In photogenerated catalysis, the photocatalytic activity (PCA) depends on the ability of the catalyst to create electron-hole pairs, which generate free radicals (hydroxyl radicals: .OH) able to undergo secondary reactions. Its comprehension has been made possible ever since the discovery of water electrolysis by means of the titanium dioxide. Commercial application of the process is called Advanced Oxidation Process (AOP). There are several methods of achieving AOP's, that can but do not necessarily involve $TiO_2$ or even the use of UV light. Generally the defining factor is the production and use of the hydroxyl radical.

When $TiO_2$ is illuminated with light of sufficient energy, electron-hole pairs are excited so that additional electrons go across the band gap to conduction band ("CB"), while holes stay in the valence band ("VB"). The excited electrons may then be used for redox reactions at the surface of $TiO_2$. There are multiple phases of $TiO_2$. For example, Rutile phase can be excited by visible light, but has a fast charge recombination rate; Anatase, on the other hand, has a slow recombination rate, but can only be excited by UV lights. Thus, it is reasonable to produce mixed phase photocatalyst to increase the total efficiency Certain titanium oxide crystalline morphologies exhibit photocatalytic characteristics when exposed to Ultra Violet (UV) light. When exposed to UV light, titanium oxide, creates electron-hole pairs which generate free radical (e.g., hydroxyl radicals). The degree of photocatalytic strength varies depending on the type of titanium oxide, for example anatase titanium oxide (particle size of about 5 to 30 nanometers) is a stronger photocatalyst than rutile titanium oxide (particle size of about 0.5 to 1 microns). Therefore, titanium oxide has potential use in sterilization, sanitation, and remediation applications.

In one embodiment of Applicants' composition and method, a titanium oxide coating including an oxidizable pigment is used with an electrostatic sprayer to produce a substantially uniform self-decontaminating coating on a surface.

Referring now to FIGS. 1, 2A, and 2B, in one embodiment, a $TiO_2$ formulation, and/or a $TiO_2$ precursor formulation in the form of a gas, liquid, aerosol, and/or solid is deposited at ambient temperature onto a surface 130. In the illustrated embodiments of FIGS. 1, 2A, and 2B, electrostatic or electrodynamic spray apparatus 100 is used to form a substantially contiguous titanium oxide containing coating 140. Using the electrostatic spray apparatus 100, the atomized particles 120 take on a first electrical charge (shown as positively charged), thereby repelling each other and spreading themselves evenly as they exit a spray nozzle 110. FIG. 2A shows a mixture 220 comprising $TiO_2$ powder in pressurized air being sprayed outwardly from a hand-held spray device 210.

Substrate 130 being coated comprises a second and opposite charge (shown as negatively charged) or grounded. The $TiO_2$ positively charged $TiO_2$ powder is then attracted to the substrate. The oppositely charged substrate attracts the $TiO_2$ powder particles, even in a "shadowed" rear portion, to give a substantially uniform coating. Use of opposing charges also increases the transfer efficiency and adhesion between the $TiO_2$ particles with the substrate. In some embodiments, the electrostatic spray apparatus may further employ pressure to produce a high-speed air stream that facilitates carrying the atomized particles 120 to the substrate 130.

In certain embodiments, the $TiO_2$ particles are charged to about 30-100 kilovolts by (a) direct charge, (b) tribo charging, or (c) post-atomization charging, for example. In a direct charging, an electrode is immersed in a supply reservoir or conduit including the $TiO_2$. In tribo charging, the inner surface area of the barrel in contact with the $TiO_2$ produces a frictional electrostatic charge as the $TiO_2$ is extruded through the electrostatic spray apparatus. In post-atomization charging, an electrostatic field is applied to the $TiO_2$ downstream of the outlet nozzle. The electrostatic field may be created by electrostatic induction or corona, for example, or by one or more electrodes (electrode ring, mesh or grid).

In certain embodiments, Applicants' composition and method utilize $TiO_2$ in combination with an organosilane comprising a quarternary ammonium moiety. In certain embodiments, that functionalized silane comprises compound 1, wherein R1 and R2 are alkyl, and wherein $X^-$ is selected from the group consisting of chloride, bromide, and iodide. Using this embodiment of Applicants' method, a target surface is coated, partially or entirely, with a mixture comprising Compound 1, and that surface is subsequently coated, partially or entirely, with $TiO_2$.

1

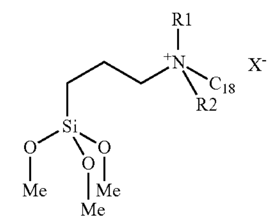

The following Examples are presented to further illustrate to persons skilled in the art how to make and use the invention. These Examples are not intended as limitations, however, upon the scope of the invention.

Example I

Two inch square formica[1] coupons were cleaned with soap and water and then isopropyl alcohol. A first group of test coupons was treated using Applicants' method wherein each test coupon was first coated electrostatically using an aqueous mixture comprising 3.6 weight percent organosilane 1. After about fifteen (15) minutes, each of these first test coupons was then electrostatically coated using an aqueous 3 weight percent colloidal suspension of $TiO_2$.

[1]Formica refers to a decorative product composed of several layers of kraft paper impregnated with melamine thermosetting resin and topped with a decorative layer protected by melamine, then compressed and cured with heat to make a hard, durable surface.

A second group of test coupons was coated electrostatically using an aqueous 3 weight percent colloidal suspension of $TiO_2$. A third group of test coupons was coated electrostatically using an aqueous mixture comprising 3.6 weight percent organosilane 1. A control group of test coupons was not coated.

The coated test coupons were then evaluated using Methicillin-resistant *Staphylococcus aureus* ("MRSA") inoculates and in accordance with ASTM E2149-10 Standard Test Method for Determining the Antimicrobial Activity of Immobilized Antimicrobial Agents Under Dynamic Contact Conditions. Table 1 recites, for each of the four groups of test coupons, an Initial MRSA Level, a 3 Hour MRSA Level, the percent MRSA remaining after three hours, and a LOG KILL.

TABLE 1

| | Applicants' Method | TiO2 ONLY | ORGANO-SILANE ONLY | CONTROL |
|---|---|---|---|---|
| Initial MRSA Level | 4.80E+07 | 1.90E+07 | 2.60E+07 | 3.00E+07 |
| 3 Hour MRSA Level | 2.50E+05 | 5.00E+05 | 3.20E+05 | 2.80E+06 |

TABLE 1-continued

|  | Applicants' Method | TiO2 ONLY | ORGANO-SILANE ONLY | CONTROL |
|---|---|---|---|---|
| Percent MRSA Remaining | 0.52 | 2.63 | 1.23 | 9.33 |
| LOG KILL | 2.3 | 1.9 | 1.6 | 1.03 |

The data of Table 1 show that use of only an organosilane coating on the test coupons resulted in about a 2.4 fold increase in the residual MRSA level after three hours compared to use of both an organosilane coating and a $TiO_2$ coating. The data of Table 1 further show that use of only a $TiO_2$ coating on the test coupons resulted in about a 5.1 fold increase in the residual MRSA level after three hours compared to use of both an organosilane coating and a $TiO_2$ coating. In summary, the data of Table 1 demonstrate that treating the test coupons with a first coating of organosilane 1 followed by a coating of $TiO_2$ was much more effective than coating the test coupons with either the organosilane only, or with TiO2 only.

Example II

A common route of transmission of cold, flu, diarrhea and other common infections is through contact with surfaces contaminated with infectious microorganisms (pathogens). Contamination occurs by settling of droplets from coughs and sneezes onto surfaces, and by touching of surfaces with hands contaminated with pathogens. The pathogens then contaminate the hands of the next person who touches the same surface, and when they bring their hands to their eyes, nose, or mouth infection can result.

Mass transportation systems create an environment in which large numbers of persons on a daily basis share space and interact with surfaces found within system vehicles. A recent study in the United Kingdom demonstrated an increase of respiratory infections (colds and flus) to persons if they had ridden in a bus or streetcar five days previously.

Application of disinfectants on surfaces has been shown to reduce absenteeism and illness in schools. Unfortunately surfaces have to be disinfected on a regular basis to be effective. There are no prior art methods that provide an effective residual property. In marked contrast to prior art methods, Applicants' method creates a surface residual, and therefore, remains effective at reducing pathogen transfer, even if the surface became re-contaminated.

Bacterial contamination of public buses with a California-based public transit authority were characterized in this study and lab analysis was used to determine the efficacy of Applicants' method to minimize exposure to microbial contaminates and odors in public spaces.

Fourteen buses were selected and divided into two groups; one an "experimental" group of seven buses that was treated with the Applicants' method; and one a "control" group of seven buses that received routine transit system treatment. Prior to any treatment, both groups where tested for heterotrophic bacteria in order to establish a baseline profile of each bus. The four-digit code for each bus was recorded.

Samples were taken at five locations in each of the fourteen busses: entry railing, fare box, driver compartment, interior railing, and seat back. Samples were taken at the end of the working day after the bus returned to the transit facility but before they were cleaned by night maintenance workers.

Sites were sampled with a Spongestick (3M, St. Paul, Minn.) containing a neutralizing broth to neutralize any disinfectant that may have been on the sampled area. Approximately 150 sq cm of the surface was sampled at each selected site in the bus.

All samples were inserted in individual bags that were labeled with a random number code. This procedure was used to prevent workers in the microbiology lab from knowing which samples belonged to which buses, thus establishing a blind study. Once the lab provided the culture results, the codes were used to assign values to the appropriate buses and locations within those buses.

The numbers of heterotrophic bacteria (HPC) were determined on R2A media (Difco, Sparks, Md.) using the spread plate method. Samples were diluted using physiological saline for assay of dilutions. All dilutions were assayed in duplicate. The agar plates were then incubated at room temperature for five days and the resulting colonies of bacteria counted.

A database was developed and all the collected data from the survey and the laboratory analytical data were entered in the database. The data was log transformed and a multiple analyses of variance (ANOVA) were conducted on the data to assess relationships between demographics and characteristics of the surfaces and their use.

Completely randomized designs were used to perform the ANOVA with a rejection region of 5% using the F distribution. Because the distribution of bacteria is not normally distributed (i.e. a bell shaped distribution curve) it is log transformed before analysis.

Log transformation is the conversion of the arithmetic number of bacteria to a log 10 (i.e. 100=2, 1,000=3, etc.). The geometric mean (average) is then determined.

Following this procedure used to establish base-line data, the experimental group of 7 buses was treated with the Applicants' method. At the end of thirty days, the same two bus groups (experimental and control) were tested to assess product effectiveness.

Total bacterial numbers or heterotrophic bacteria on hard surfaces are used as a general measure of the sanitization of public surfaces and the effectiveness of cleaning and disinfection of surfaces. The number of bacteria per 150 sq. cm ranged from 80 to 17,200,000 on the surfaces tested. The geometric average number of bacteria in the buses used in this study is shown in Table 2.

Geometric averages are always lower than arithmetic averages as they normalize high and low values. The statistical analysis indicated that there was no statistical difference in the numbers of bacteria in the busses that were selected for treatment and those that were not at the beginning (baseline data) of the study.

TABLE 2

Occurrence of Bacteria in Treated vs. Untreated Buses at Baseline (Day 0 - before treatment of experimental buses)

| | $Log_{10}$ | | Arithmetic | |
|---|---|---|---|---|
| Parameter | Treated* | Control | Treated | Control |
| Number of Samples | 35 | 35 | 35 | 35 |
| Geometric Mean | 2.89 | 3.13 | 776 | 1,349 |
| St. Dev. | 1.13 | 0.75 | 12.3 | 14.5 |

*buses selected for treatment before treatment was applied

After 30 days, data reported in Table 3A demonstrate that there was a significant difference (p=0.005) i.e., a 99.95% probability that there is a difference in the geometric average number of bacteria in the treated and untreated buses. The number of bacteria in the treated buses was significantly less than that found in the untreated buses 30 days after treatment. On average there were 93% fewer bacteria on the surfaces in the treated buses vs. the untreated buses.

TABLE 3A

Bacterial Concentrations in Treated vs. Untreated Buses After 30 Days

| Parameter | $Log_{10}$ | | Arithmetic | |
| --- | --- | --- | --- | --- |
| | Treated | Control | Treated | Control |
| Number of Samples | 35 | 25* | 35 | 25* |
| Geometric Mean | 3.77 | 4.92 | 5,888 | 83,176 |
| St. Dev. | 1.69 | 1.58 | 48.9 | 38.0 |

*two buses in the control group had been removed from service

The results of Table 3A demonstrate a significant difference between the bacterial load in the [bus] interior of the treated and untreated buses. With the exception of the entry railing, the bacterial burden at all treated sites was reduced as compared to the untreated sites.

The concentration of bacteria at specific sites tested in treated and untreated busses is shown in Table 4 below. The greatest difference between treated and untreated buses in bacteria numbers was in the driver's compartment where there were fewer than 99.8% bacteria in the treated busses. This difference was highly significant (p=0.007).

It appears that the inordinate wear and tear from passenger contact friction on the entrance railings removed Applicants' coating at those places. Table 3B recites the experimental data excluding this site (entrance railing) as an outlier.

After 30 days, with this site excluded, there was a significant difference (p=0.001 i.e. a 99.99% probability that there is a difference) (Table 3B) in the geometric average number of bacteria in the treated and untreated buses. On average there were 97% fewer bacteria on the surfaces in the treated buses vs. the untreated buses.

TABLE 3B

Bacterial Concentrations in Treated vs. Untreated Buses after 30 Days (Entry Railing Excluded)

| Parameter | $Log_{10}$ | | Arithmetic | |
| --- | --- | --- | --- | --- |
| | Treated | Control | Treated | Control |
| Number of Samples | 28 | 20* | 28 | 20* |
| Geometric Mean | 3.42 | 4.91 | 2,630 | 81,283 |
| St. Dev. | 1.48 | 1.52 | 30.2 | 33.1 |

*two buses in the control group had been removed from service

TABLE 4

Bacterial Concentrations at Specific Tested Sites in Treated and Untreated Buses

| Site | Treated Bus | | Untreated Bus | | % reduction | p |
| --- | --- | --- | --- | --- | --- | --- |
| | Log10 | Arithmetic | Log10 | Arithmetic | | |
| Drivers Compartment | 2.91 | 812.8 | 5.56 | 363,078 | 99.8 | 0.007 |
| Entrance Railing | 5.18 | 151,356 | 4.96 | 91,201 | 0 | 0.75 |
| Seat Backs | 2.84 | 692.8 | 4.49 | 30,903 | 97.8 | 0.071 |
| Interior Railing | 3.36 | 2,291 | 4.25 | 17,783 | 87.1 | 0.222 |
| Fare Box | 4.56 | 36,307 | 5.49 | 309,029 | 88.3 | 0.253 |

This Example II shows that at the beginning of the study there was no statistical difference between levels of bacteria in the buses selected for study. This Example II further shows that the concentration of bacteria was significantly less in the interior of the treated vs. untreated buses after 30 days of use. On average there were 97% fewer bacteria on the interior surfaces of the treated buses in comparison to the same surfaces of the untreated surfaces.

In certain embodiments, Applicants' method utilizes $TiO_2$ in combination with an oxidizable pigment. In certain embodiments, the oxidizable pigment comprises Methylene Blue, Compound 10. The $TiO_2$ is deposited upon the substrate, using a conventional spray means or an electrostatic spray apparatus (collectively the "spray apparatus"). Portions of the substrate coated with the $TiO_2$ particles visually display the color of the oxidizable pigment. For example, portions of the substrate coated with $TiO_2$ particles/Methylene Blue mixture visually appear blue.

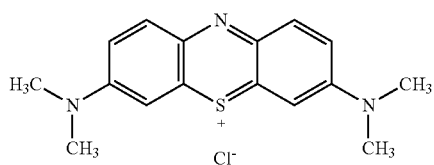

10

In marked contrast, portions of the substrate not coated with the $TiO_2$ particles do not display the color. A second coating application can be applied to the non-colored portions of the substrate for a more uniform deposition of the $TiO_2$ particles. Exposure of the $TiO_2$ particles to UV light then produces free radicals that oxidize the oxidizable pigment. As a result, a substantially contiguous titanium oxide coating is formed on the substrate, and that coating becomes translucent or white.

Figure 2A:
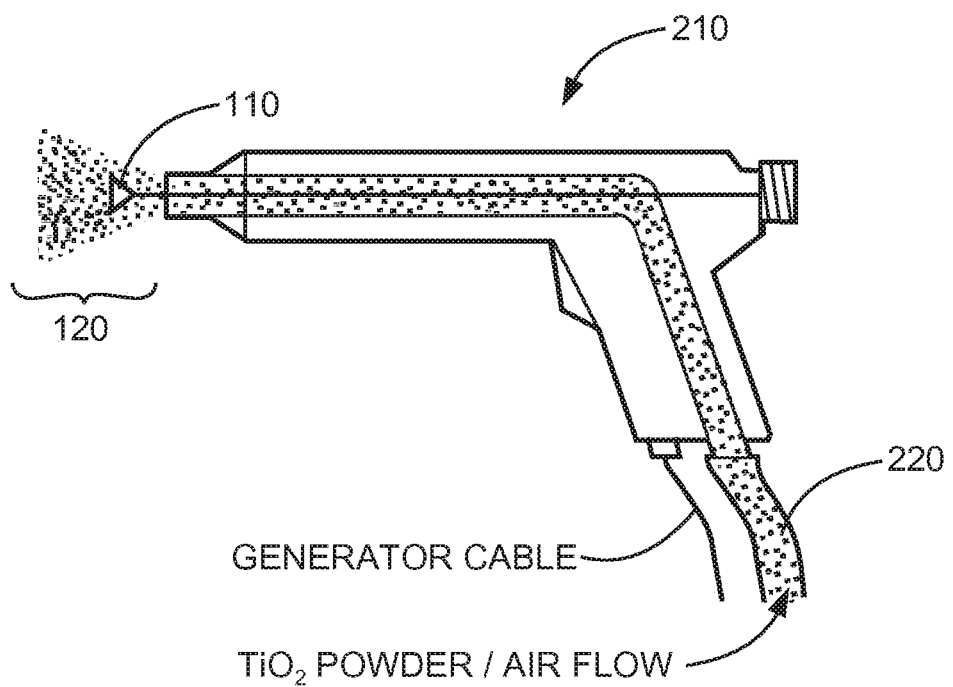
FIG. 2A illustrates another embodiment of a electrostatic spray apparatus.
Figure 2B:
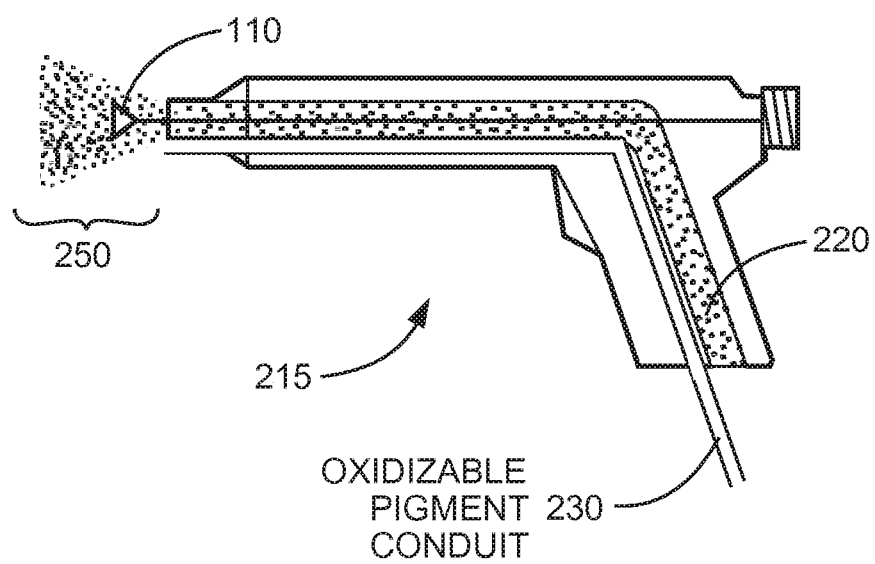
FIG. 2B illustrates the electrostatic spray apparatus of FIG. 2A further comprising a source of oxidizable pigment.

To illustrate, Methylene Blue pigment may be added to the $TiO_2$. In certain embodiments, the Methylene Blue is added directly into the $TiO_2$ powder. In other embodiments, the Methylene Blue is delivered to a nozzle portion of a spray apparatus via an air stream separate from an airstream carrying the $TiO_2$ powder. For example and referring to FIG. 2B, electrostatic hand-held spray device 215 comprises an oxidizable pigment conduit 230. An oxidizable pigment, such as for example Methylene Blue, is discharged from device 215 in combination with $TiO_2$ powder to form a spray 250 comprising charged $TiO_2$ particle and charged Methylene Blue molecules.

The degradation of Methylene Blue after deposition of a TiO$_2$ coating on a substrate is effected by the interaction with the electron-hole pair (e-CB–h+VB). Houas A, Lachheb H, Ksibi M, Elaloui E, Guillard C, andHerrman J-M, Photocatalytic degradation pathway of Methylene Blue in water. Appl Catal B 31, 145-57 (2001) proposed the mechanism of Scheme I.

Scheme I

1. TiO$_2$+photon→e-CB+h+VB

2. O$_2$(ads)+e-CB→O$_2$.—

3. (H$_2$O↔H++OH—)(ads)+h+VB→H++.OH

4. O$_2$.—+H+→HO$_2$.

5. 2HO$_2$.→H$_2$O$_2$+O2

6. H$_2$O$_2$+e-→.OH+OH—

7. Methylene Blue(ads)+.OH→degradation products

In step (2) of Scheme I, O$_2$(ads) comes from ambient O2 present in the system and was adsorbed onto the surface of the TiO$_2$. Methylene Blue has a cationic configuration thus it should be favorably adsorbed to the negative sites of the h-TiO$_2$ surface, e.g., Ti—O(-) and subsequently attacked by the very active .OH moiety, leading to the destruction of the Methylene Blue molecule.

Various embodiments of Applicants' method and composition provide a titanium alkoxide starting material (RO)$_4$Ti photocatalyst surface coating precursor. For example, in certain embodiments Applicants' method forms a liquid coating composition using titanium tetraisopropoxide 2, and casts that coating composition solution onto a surface to form a coating comprising a linear polymeric structure 3 on the surface.

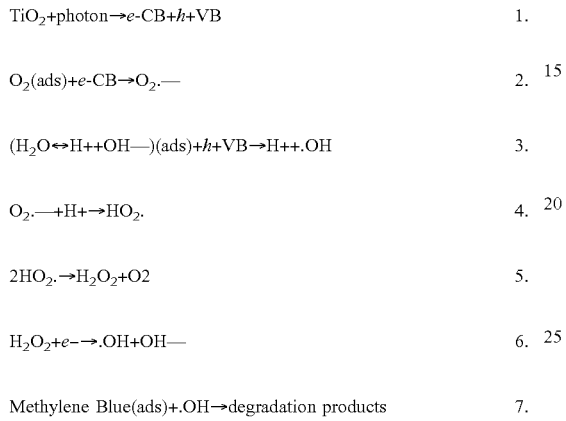

In other embodiments, Applicants' method forms a liquid coating composition using titanium tetraisopropoxide 2, and casts that coating composition solution onto a surface to form a coating comprising a cross-linked structure 4 on the surface.

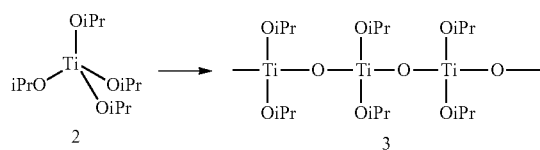

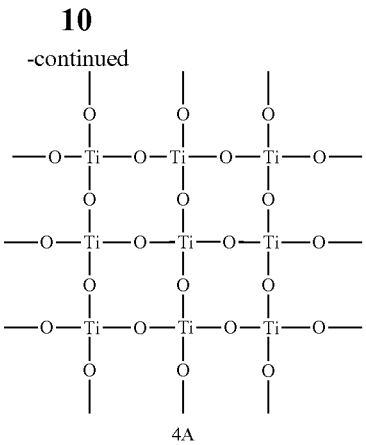

4A

The following Example III is presented to further illustrate to persons skilled in the art how to make and use the invention. This example is not intended as a limitation, however, upon the scope of the invention.

Example III 9.0 grams of tartaric acid were dissolved in 0.120 liters of water in an Erlynmeyer flask to give a 0.5 molar solution. This solution was stirred overnight at room temperature. The following day, the tartaric acid solution was filtered through filter paper (Whatman #1), then subsequently through a 0.2 micron PRFW filter to remove particulates. 25 mL of filtered 0.5 M tartaric acid (0.01249 moles of tartaric acid) was poured into a round bottom flask and chilled on ice with stirring. 3.69 grams of titanium (IV) isopropoxide was added slowly first with a 1 mL addition. 1 mL aliquots of titanium (IV) isopropoxide were added until all of it was added to the tartaric acid solution.

Upon addition of the titanium (IV) isopropoxide the ice bath was removed. The solution remained a solution for approximately 10 minutes after which it became a clear gel and became progressively opaque (white). The gel was stirred at RT overnight. The gelatinous material was mixed with water, or isopropanol and water, and then cast onto a glass surface to form a coating thereon. In certain embodiments, Applicants' coating of this Example II comprises a tartaric acid/titanium isopropoxide repeat unit 11A, wherein (r) is between 1 and about 10. In certain embodiments, Applicants' coating of this Example III comprises a tartaric acid/titanium isopropoxide adduct 11B.

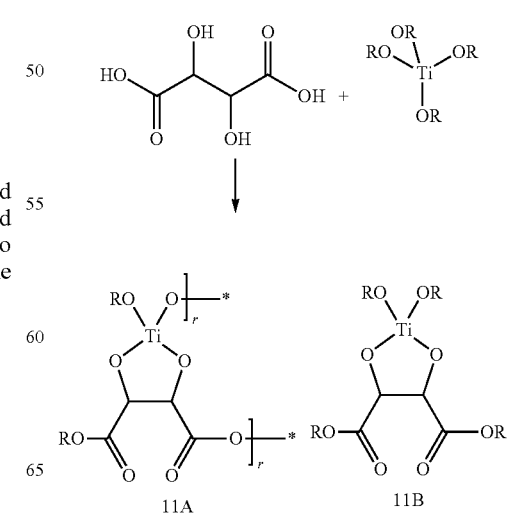

11A      11B

In other embodiments, Applicants' coating composition comprises one or more hydroxyl acids other than tartaric acid in combination with TiO$_2$. In certain embodiments, these one or more hydroxyl acids include one or more alpha hydroxyl acids including glycolic acid, lactic acid, citric acid, and/or mandelic acid. In certain embodiments, these one or more hydroxyl acids include one or more beta hydroxyl acids including salicyclic acid and/or beta-hydroxypropionic acid.

Figure 3:
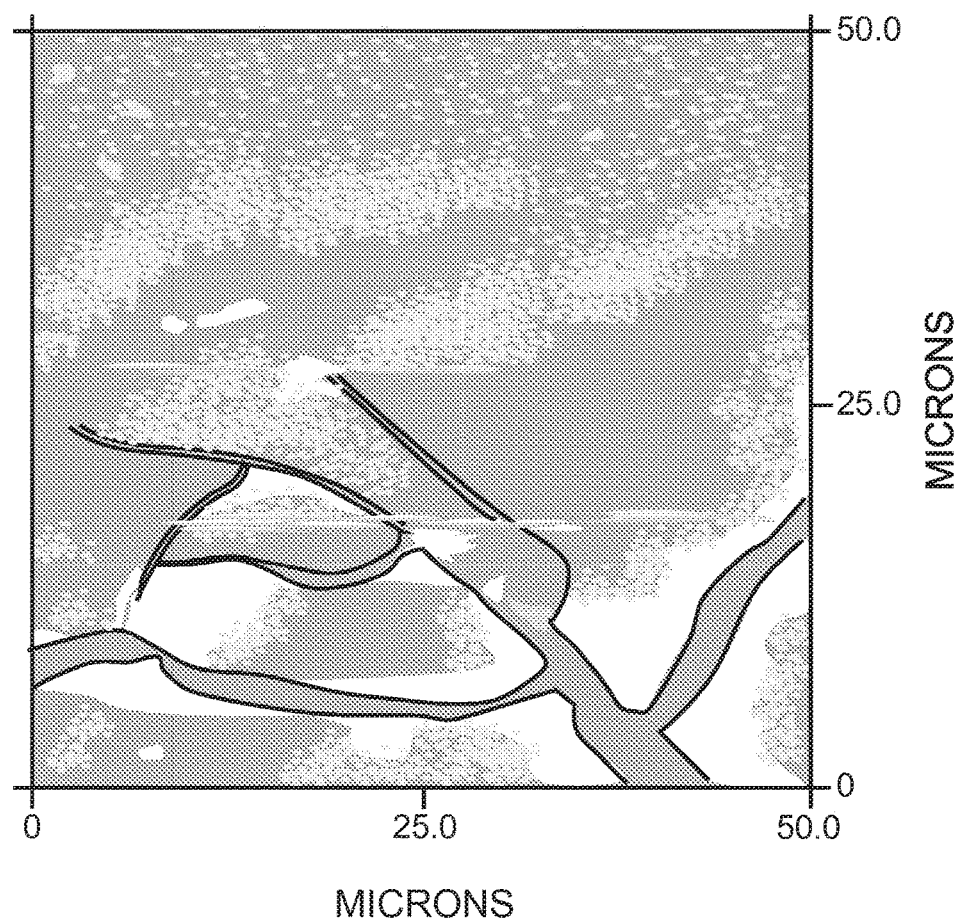
FIG. 3 is an Atomic Force Microscope image at 50 microns showing a coating on a glass surface, where that coating was formed using Applicants' composition and method.
Figure 4:
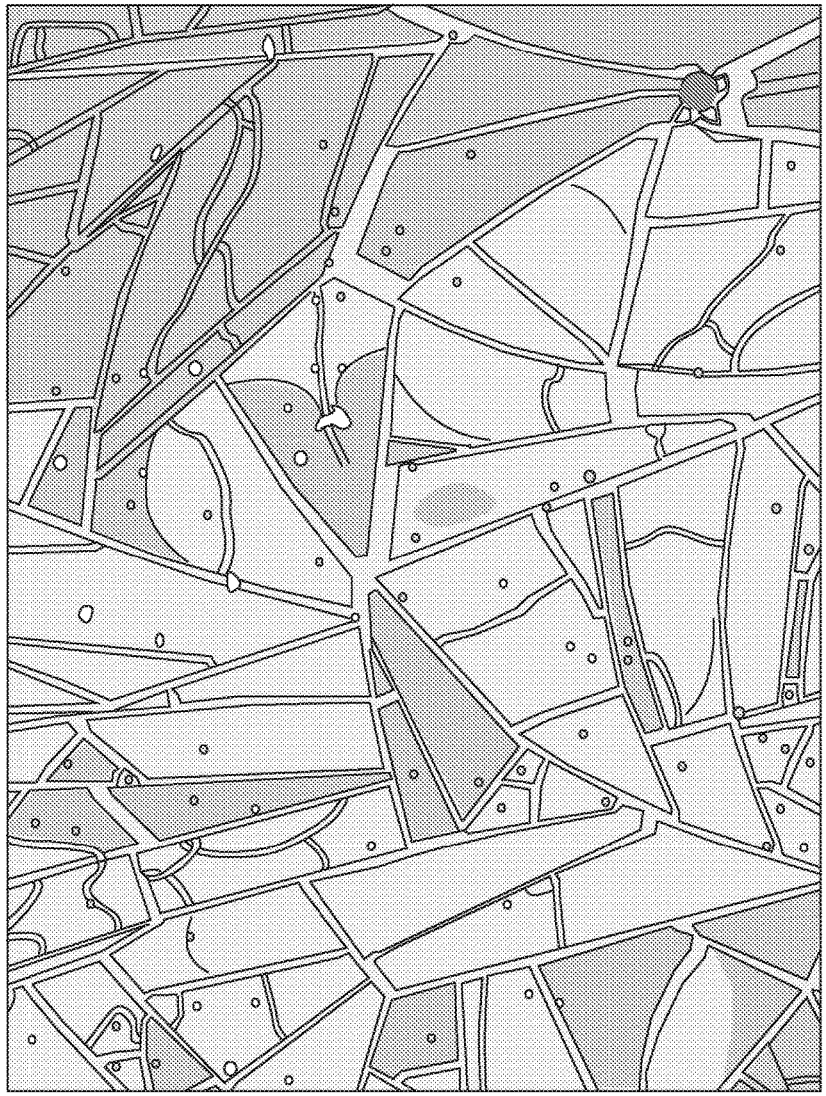
FIG. 4 is an optical image using transmission geometry with 10× objective showing a coating on a glass surface, where that coating was formed using Applicants' composition and method.

FIGS. 3 and 4 show images of the coating formed on the glass surface. FIG. 3 is an Atomic Force Microscope image at 50 microns. FIG. 4 is an optical image using transmission geometry with 10× objective.

In certain embodiments, Applicants utilize silane alkoxide 5, wherein silane alkoxide 5 comprises a quaternary ammonium salt. In certain embodiments, R5 is selected from the group alkyl, and oxyalkyl. In certain embodiments, R6 is selected from the group consisting of alkyl, alkenyl, phenyl, and benzyl. In certain embodiments, R7 is selected from the group consisting of alkyl, alkenyl, phenyl, and benzyl. In certain embodiments, R8 is selected from the group consisting of alkyl, alkenyl, phenyl, and benzyl. In certain embodiments, R8 comprises C18 alkyl.

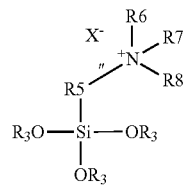

5

In certain embodiments, an embodiment of Compound 5 is prepared from choline 12 and silyl ester 13 to form an ammonium silyl ester 14, wherein (p) is between 1 and about 5, and wherein R is selected from the group consisting of methyl and ethyl.

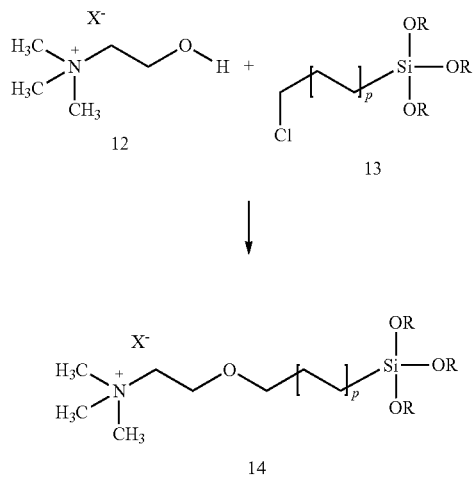

In certain embodiments, Applicants' method prepares a polymeric material 6 and/or polymeric material 8 using titanium alkoxide monomer 2 and silane alkoxide monomer 5.

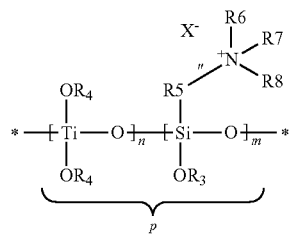

6

In certain embodiments, Applicant utilize Titanium alkoxide 7 to prepare a self-decontaminating coating.

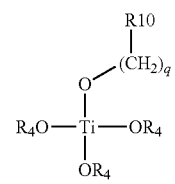

7

In certain embodiments, q is between 1 and about 10. In certain embodiments, R10 comprises a chromophore that upon exposure of electromagnetic radiation having a first frequency emits electromagnetic radiation having a second frequency, wherein the second frequency differs from the first frequency. In certain embodiments, the first frequency is within the ultraviolet spectrum and the second frequency is within the visible spectrum. Those of ordinary skill in the art will appreciate that a typical human eye will respond to wavelengths from about 390 to 750 nm.

Figure 5:
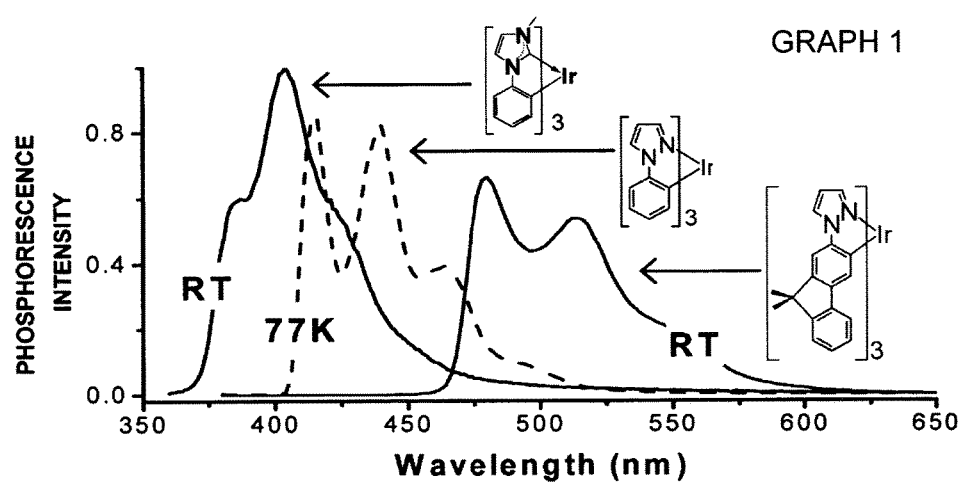
FIG. 5 is an emission spectra for three different triscyclometalated iridium(III) materials.

In certain embodiments, R10 comprises a triscyclometalated iridium(III) material that, upon UV irradiation, emits light in the visible spectrum. Graph 1, see FIG. 5, shows the emission spectra for three different triscyclometalated iridium(III) materials.

In certain embodiments, Applicants' method prepares a polymeric material 8 using titanium alkoxide monomer 2 and silane alkoxide monomer 7. In certain embodiments, Applicants polymeric material 8 is prepared from polymeric material 6.

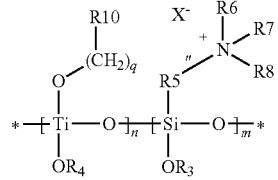

8

In certain embodiments, Applicants prepare a polymeric material 6 and/or polymeric material 8 wherein n=0, p=1, and m=1 to about 500. In certain embodiments, Applicants prepare a polymeric material 6 and/or polymeric material 8 wherein m=0, p=1, and n is 1 to about 500.

In certain embodiments, Applicants' method disposes a first coating on a surface wherein said first coating comprises polymeric material 6 and/or polymeric material 8 wherein n=0, p=1, and m=1 to about 500. In certain embodiments, the first coating is applied using the electrostatic spray assembly of FIG. 2A and/or FIG. 2B. Applicants' method then disposes a second coating on the same surface over the first coating, wherein the second coating comprises polymeric material 6 and/or polymeric material 8 wherein m=0, p=1, and n=1 to about 500. In certain embodiments, the second coating is applied using the electrostatic spray assembly of FIG. 2A and/or FIG. 2B.

In certain embodiments, Applicants prepare a polymeric material 6 and/or polymeric material 8 wherein n is between about 5 and 500, and wherein m is 1, and wherein p is 1. In certain embodiments, Applicants prepare a polymeric material 6 and/or polymeric material 8 wherein n is between about 5 and 500, and wherein m is 2, and wherein p is 1, such that polymeric material 6 and/or polymeric material 8 comprises a titanium/oxygen backbone with silyl ester end groups. In certain embodiments, Applicants prepare a polymeric material 6 and/or polymeric material 8 wherein n is between about 5 and 500, and wherein m is 2, and wherein p is 1, such that polymeric material 6 and/or polymeric material 8 comprises a titanium/oxygen backbone with silyl ester end groups, wherein that polymeric material comprises a substantially linear structure. In certain embodiments, Applicants prepare a polymeric material 6 and/or polymeric material 8 wherein n is between about 5 and 500, and wherein m is 2, and wherein p is 1, such that polymeric material 6 and/or polymeric material 8 comprises a titanium/oxygen backbone with silyl ester end groups, wherein that polymeric material comprises a cross-linked structure.

In certain embodiments, Applicants prepare a polymeric material 6 and/or polymeric material 8 wherein m is between about 5 and 500, and wherein n is 1 and wherein p is 1. In certain embodiments, Applicants prepare a polymeric material 6 and/or polymeric material 8 wherein m is between about 5 and 500, and wherein n is 2, and wherein p is 1, such that polymeric material 6 and/or polymeric material 8 comprises a silicone/oxygen backbone with titanyl ester end groups.

In certain embodiments, Applicants prepare a polymeric material 6 and/or polymeric material 8 wherein m is between about 5 and 500, and wherein n is 2, and wherein p is 1, such that polymeric material 6 and/or polymeric material 8 comprises a silicone/oxygen backbone with titanyl ester end groups, wherein that polymeric material comprises a substantially linear structure. In certain embodiments, Applicants prepare a polymeric material 6 and/or polymeric material 8 wherein m is between about 5 and 500, and wherein n is 2, and wherein p is 1, such that polymeric material 6 and/or polymeric material 8 comprises a silicone/oxygen backbone with titanyl ester end groups, wherein that polymeric material comprises a cross-linked structure.

Applicants method includes forming a coating composition comprising a polymeric material 6 and/or polymeric material 8 wherein m is between about 5 and 500, and wherein n is 2, and wherein p is 1, and casting that coating composition onto a substrate to form a self-decontaminating surface on that substrate. Applicants method includes forming a coating composition comprising a polymeric material 6 and/or polymeric material 8 wherein n is between about 5 and 500, and wherein m is 2, and wherein p is 1, and casting that coating composition onto a substrate to form a self-decontaminating surface on that substrate.

In certain embodiments, Applicants prepare a polymeric material 6 and/or polymeric material 8 wherein n is between about 1 and 10, and wherein m is between about 1 and 10, and wherein p is between about 1 and 10. In certain embodiments, Applicants prepare a polymeric material 6 and/or polymeric material 8 wherein n is between about 1 and 10, and wherein m is between about 1 and 10, and wherein p is between about 1 and 10, such that the polymeric material comprises titanyl ester end groups, wherein that polymeric material comprises a substantially linear structure. In certain embodiments, Applicants prepare a polymeric material 6 and/or polymeric material 8 wherein n is between about 1 and 10, and wherein m is between about 1 and 10, and wherein p is between about 1 and 10, such that the polymeric material comprises titanyl ester end groups, wherein that polymeric material comprises a cross-linked structure.

In certain embodiments, Applicants prepare a polymeric material 6 and/or polymeric material 8 wherein n is between about 1 and 10, and wherein m is between about 1 and 10, and wherein p is between about 1 and 10, such that the polymeric material comprises silyl ester end groups, wherein that polymeric material comprises a substantially linear structure.

In certain embodiments, Applicants prepare a polymeric material 6 and/or polymeric material 8 wherein n is between about 1 and 10, and wherein m is between about 1 and 10, and wherein p is between about 1 and 10, such that the polymeric material comprises silyl ester end groups, wherein that polymeric material comprises a cross-linked structure.

Applicants method includes forming a coating composition comprising a polymeric material 6 and/or polymeric material 8 wherein n is between about 1 and 10, and wherein m is between about 1 and 10, and wherein p is between about 1 and 10, such that the polymeric material comprises silyl ester end groups, and casting that coating composition onto a substrate to form a self-decontaminating surface on that substrate. Applicants method includes forming a coating composition comprising a polymeric material 6 and/or polymeric material 8 wherein n is between about 1 and 10, and wherein m is between about 1 and 10, and wherein p is between about 1 and 10, such that the polymeric material comprises titanyl ester end groups, and casting that coating composition onto a substrate to form a self-decontaminating surface on that substrate.

In certain embodiments, Applicants' coating composition is embodied in a flexible, planar member to form a composite disinfecting wipe. Applicants' composite disinfecting wipe is capable of cleaning and removing residues from soiled surfaces while simultaneously destroying undesirable microorganisms, e.g. bacteria, mold, viruses, prions and the like that colonize on common surfaces with which people come into contact, such as doorknobs, countertops, toilet seats, floors, beds, walls, and the like.

While the preferred embodiments of the present invention have been illustrated in detail, it should be apparent that modifications and adaptations to those embodiments may occur to one skilled in the art without departing from the scope of the present invention as set forth herein.

We claim:

1. A coating composition comprising:
an organosilane of structure (5),

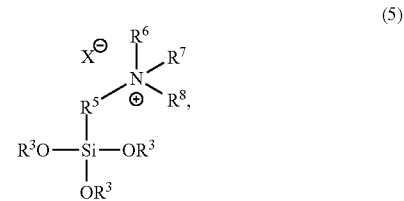

(5)

wherein $R^3$ is alkyl; $R^5$ is selected from the group consisting of alkyl and oxyalkyl; $R^6$, $R^7$, and $R^8$ are selected from the group consisting of alkyl, alkenyl, phenyl, and benzyl; and $X^-$ is selected from the group consisting of chlorine, bromine, and iodine; and titanium (IV) isopropoxide.

2. The composition of claim 1, wherein said organosilane is an organosilane of structure (1),

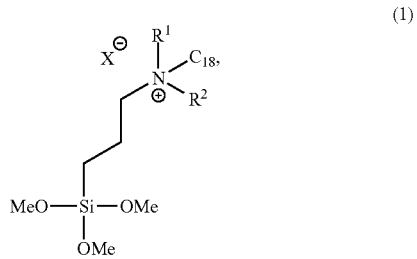

(1)

wherein $R^1$ and $R^2$ are alkyl, and $X^-$ is selected from the group consisting of chlorine, bromine, and iodine.

3. The composition of claim 1, wherein said organosilane is an organosilane of structure (14),

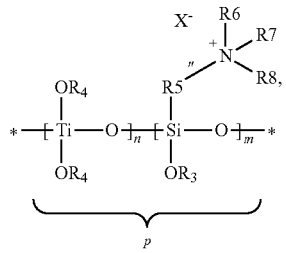

(14)

wherein R is selected from the group consisting of methyl and ethyl; $X^-$ is selected from the group consisting of chlorine, bromine, and iodine; and p is from 1 to 5.

4. The composition of claim 1, wherein $R^8$ comprises a $C_{18}$ alkyl chain.

5. The composition of claim 1, wherein said organosilane and said titanium (IV) isopropoxide react to form a polymer of structure (6),

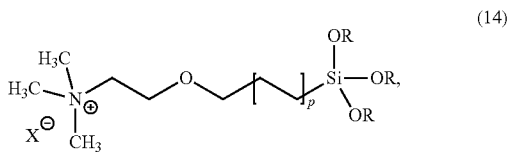

6 wherein $R^3$ is alkyl; $R^4$ is isopropyl; $R^5$ is selected from the group consisting of alkyl and oxyalkyl; $R^6$, $R^7$, and $R^8$ are selected from the group consisting of alkyl, alkenyl, phenyl, and benzyl; and $X^-$ is selected from the group consisting of chlorine, bromine, and iodine; m is between about 5 and 500; n is 2; and p is 1.

6. The composition of claim 5, wherein $R^3$ is alkyl; $R^4$ is isopropyl; $R^5$ is selected from the group consisting of alkyl and oxyalkyl; $R^6$, $R^7$, and $R^8$ are selected from the group consisting of alkyl, alkenyl, phenyl, and benzyl; and $X^-$ is selected from the group consisting of chlorine, bromine, and iodine; m is 1; n is between about 5 and 500; and p is 1.

7. The composition of claim 5, wherein $R^3$ is alkyl; $R^4$ is isopropyl; $R^5$ is selected from the group consisting of alkyl and oxyalkyl; $R^6$, $R^7$, and $R^8$ are selected from the group consisting of alkyl, alkenyl, phenyl, and benzyl; and $X^-$ is selected from the group consisting of chlorine, bromine, and iodine; m is 2; n is between about 5 and 500; and p is 1, such that polymer (6) comprises a titanium/oxygen backbone with silyl ester end groups.

8. The composition of claim 5, wherein $R^3$ is alkyl; $R^4$ is isopropyl; $R^5$ is selected from the group consisting of alkyl and oxyalkyl; $R^6$, $R^7$, and $R^8$ are selected from the group consisting of alkyl, alkenyl, phenyl, and benzyl; and $X^-$ is selected from the group consisting of chlorine, bromine, and iodine; m is between about 5 and 500; n is 2; and p is 1, such that polymer (6) comprises a titanium/oxygen backbone with silyl ester end groups, and wherein polymer (6) is substantially linear.

9. The composition of claim 5, wherein $R^3$ is alkyl; $R^4$ is isopropyl; $R^5$ is selected from the group consisting of alkyl and oxyalkyl; $R^6$, $R^7$, and $R^8$ are selected from the group consisting of alkyl, alkenyl, phenyl, and benzyl; and $X^-$ is selected from the group consisting of chlorine, bromine, and iodine; m is 2; n is between about 5 and 500; and p is 1, such that polymer (6) comprises a titanium/oxygen backbone with silyl ester end groups, and wherein polymer (6) is comprises a cross-linked structure.

10. The composition of claim 5, wherein $R^3$ is alkyl; $R^4$ is isopropyl; $R^5$ is selected from the group consisting of alkyl and oxyalkyl; $R^6$, $R^7$, and $R^8$ are selected from the group consisting of alkyl, alkenyl, phenyl, and benzyl; and $X^-$ is selected from the group consisting of chlorine, bromine, and iodine; m is between about 5 and 500; n is 1; and p is 1.

11. The composition of claim 5, wherein $R^3$ is alkyl; $R^4$ is isopropyl; $R^5$ is selected from the group consisting of alkyl and oxyalkyl; $R^6$, $R^7$, and $R^8$ are selected from the group consisting of alkyl, alkenyl, phenyl, and benzyl; and $X^-$ is selected from the group consisting of chlorine, bromine, and iodine; m is between about 5 and 500; n is 2; and p is 1, such that polymer (6) comprises a silicone/oxygen backbone with titanyl ester end groups.

12. The composition of claim 11, wherein polymer (6) is substantially linear.

13. The composition of claim 11, wherein polymer (6) comprises a cross-linked structure.

14. A self-decontaminating surface on a substrate formed by casting the coating composition of claim 11 onto the substrate.

15. The composition of claim 5, wherein $R^3$ is alkyl; $R^4$ is isopropyl; $R^5$ is selected from the group consisting of alkyl and oxyalkyl; $R^6$, $R^7$, and $R^8$ are selected from the group consisting of alkyl, alkenyl, phenyl, and benzyl; and $X^-$ is selected from the group consisting of chlorine, bromine, and iodine; m is between about 1 and 10; n is between about 1 and 10; and p is between about 1 and 10, such that polymer (6) comprises titanyl ester end groups.

16. The composition of claim 15, wherein polymer (6) is substantially linear or comprises a cross-linked structure.

17. The composition of claim 5, wherein $R^3$ is alkyl; $R^4$ is isopropyl; $R^5$ is selected from the group consisting of alkyl and oxyalkyl; $R^6$, $R^7$, and $R^8$ are selected from the group consisting of alkyl, alkenyl, phenyl, and benzyl; and $X^-$ is selected from the group consisting of chlorine, bromine, and iodine; m is between about 1 and 10; n is between about 1 and 10; and p is between about 1 and 10, such that polymer (6) comprises silyl ester end groups.

18. A self-decontaminating surface on a substrate formed by casting the coating composition of claim 17 onto the substrate.

19. The composition of claim 5, wherein $R^3$ is alkyl; $R^4$ is isopropyl; $R^5$ is selected from the group consisting of alkyl and oxyalkyl; $R^6$, $R^7$, and $R^8$ are selected from the group consisting of alkyl, alkenyl, phenyl, and benzyl; and $X^-$ is selected from the group consisting of chlorine, bromine, and iodine; m is between about 1 and 10; n is between about 1 and 10; and p is between about 1 and 10, such that polymer (6) comprises titanyl ester end groups.

20. A self-decontaminating surface on a substrate formed by casting the coating composition of claim 19 onto the substrate.

* * * * *